(12) United States Patent
Hoarau et al.

(10) Patent No.: US 8,060,171 B2
(45) Date of Patent: Nov. 15, 2011

(54) MEDICAL SENSOR FOR REDUCING MOTION ARTIFACTS AND TECHNIQUE FOR USING THE SAME

(75) Inventors: Carine Hoarau, Lafayette, CA (US); Clark R. Baker, Jr., Castro Valley, CA (US); Edward Karst, South Pasadena, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 658 days.

(21) Appl. No.: 11/497,089

(22) Filed: Aug. 1, 2006

(65) Prior Publication Data

US 2007/0073128 A1  Mar. 29, 2007

Related U.S. Application Data

(63) Continuation of application No. 11/241,375, filed on Sep. 29, 2005.

(51) Int. Cl.
*A61B 5/1455* (2006.01)
(52) U.S. Cl. .............................. 600/323; 600/344
(58) Field of Classification Search .................. 600/322, 600/323, 344
See application file for complete search history.

(56) References Cited

U.S. PATENT DOCUMENTS

| | | | |
|---|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsey et al. |
| D262,488 S | 12/1981 | Rossman et al. |
| 4,321,930 A | 3/1982 | Jobsis et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,510,938 A | 4/1985 | Jobsis et al. |

(Continued)

FOREIGN PATENT DOCUMENTS

CN  11080192  11/2007

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

(Continued)

*Primary Examiner* — Eric Winakur
(74) *Attorney, Agent, or Firm* — Fletcher Yoder

(57) ABSTRACT

A sensor for pulse oximetry or other applications utilizing spectrophotometry may be adapted to reduce motion artifacts by fixing the optical distance between an emitter and detector. A flexible sensor is provided with a stiffening member to hold the emitter and detector of the sensor in a relatively fixed position when applied to a patient. Further, an annular or partially annular sensor is adapted to hold an emitter and detector of the sensor in a relatively fixed position when applied to a patient. A clip-style sensor is provided with a spacer that controls the distance between the emitter and detector.

21 Claims, 8 Drawing Sheets

U.S. PATENT DOCUMENTS

| | | |
|---|---|---|
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,039 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,348,005 A | 9/1994 | Merrick et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |

| | | | | | |
|---|---|---|---|---|---|
| 5,355,880 A | 10/1994 | Thomas et al. | 5,619,991 A | 4/1997 | Guthrie et al. |
| 5,355,882 A | 10/1994 | Ukawa et al. | 5,619,992 A | 4/1997 | Guthrie et al. |
| 5,361,758 A | 11/1994 | Hall et al. | 5,626,140 A | 5/1997 | Feldman et al. |
| 5,365,066 A | 11/1994 | Krueger, Jr. et al. | 5,630,413 A | 5/1997 | Thomas et al. |
| 5,368,025 A | 11/1994 | Young et al. | 5,632,272 A | 5/1997 | Diab et al. |
| 5,368,026 A | 11/1994 | Swedlow et al. | 5,632,273 A | 5/1997 | Suzuki |
| 5,368,224 A | 11/1994 | Richardson et al. | 5,634,459 A | 6/1997 | Gardosi |
| 5,372,136 A | 12/1994 | Steuer et al. | 5,638,593 A | 6/1997 | Gerhardt et al. |
| 5,377,675 A | 1/1995 | Ruskewicz et al. | 5,638,816 A | 6/1997 | Kiani-Azarbayjany et al. |
| 5,385,143 A | 1/1995 | Aoyagi | 5,638,818 A | 6/1997 | Diab et al. |
| 5,387,122 A | 2/1995 | Goldberger et al. | 5,645,060 A | 7/1997 | Yorkey et al. |
| 5,390,670 A | 2/1995 | Centa et al. | 5,645,440 A | 7/1997 | Tobler et al. |
| 5,392,777 A | 2/1995 | Swedlow et al. | 5,660,567 A | 8/1997 | Nierlich et al. |
| 5,398,680 A | 3/1995 | Polson et al. | 5,662,105 A | 9/1997 | Tien |
| 5,402,777 A | 4/1995 | Warring et al. | 5,662,106 A | 9/1997 | Swedlow et al. |
| 5,402,779 A | 4/1995 | Chen et al. | 5,664,270 A | 9/1997 | Bell et al. |
| 5,411,023 A | 5/1995 | Morris, Sr. et al. | 5,666,952 A | 9/1997 | Fuse et al. |
| 5,411,024 A | 5/1995 | Thomas et al. | 5,671,529 A | 9/1997 | Nelson |
| 5,413,099 A | 5/1995 | Schmidt et al. | 5,673,692 A | 10/1997 | Schulze et al. |
| 5,413,100 A | 5/1995 | Barthelemy et al. | 5,673,693 A | 10/1997 | Solenberger |
| 5,413,101 A | 5/1995 | Sugiura | 5,676,139 A | 10/1997 | Goldberger et al. |
| 5,413,102 A | 5/1995 | Schmidt et al. | 5,676,141 A | 10/1997 | Hollub |
| 5,417,207 A | 5/1995 | Young et al. | 5,678,544 A | 10/1997 | DeLonzor et al. |
| 5,421,329 A | 6/1995 | Casciani et al. | 5,680,857 A | 10/1997 | Pelikan et al. |
| 5,425,360 A | 6/1995 | Nelson | 5,685,299 A | 11/1997 | Diab et al. |
| 5,425,362 A | 6/1995 | Siker et al. | 5,685,301 A | 11/1997 | Klomhaus |
| 5,427,093 A | 6/1995 | Ogawa et al. | 5,687,719 A | 11/1997 | Sato et al. |
| 5,429,128 A | 7/1995 | Cadell et al. | 5,687,722 A | 11/1997 | Tien et al. |
| 5,429,129 A | 7/1995 | Lovejoy et al. | 5,692,503 A | 12/1997 | Kuenstner |
| 5,431,159 A | 7/1995 | Baker et al. | 5,692,505 A | 12/1997 | Fouts |
| 5,431,170 A | 7/1995 | Mathews | 5,709,205 A | 1/1998 | Bukta |
| 5,437,275 A | 8/1995 | Amundsen et al. | 5,713,355 A | 2/1998 | Richardson et al. |
| 5,438,986 A | 8/1995 | Disch et al. | 5,724,967 A | 3/1998 | Venkatachalam |
| 5,448,991 A | 9/1995 | Polson et al. | 5,727,547 A | 3/1998 | Levinson et al. |
| 5,452,717 A | 9/1995 | Branigan et al. | 5,730,124 A | 3/1998 | Yamauchi |
| 5,465,714 A | 11/1995 | Scheuing | 5,731,582 A | 3/1998 | West |
| 5,469,845 A | 11/1995 | DeLonzor et al. | D393,830 S | 4/1998 | Tobler et al. |
| RE35,122 E | 12/1995 | Corenman et al. | 5,743,260 A | 4/1998 | Chung et al. |
| 5,482,034 A | 1/1996 | Lewis et al. | 5,743,262 A | 4/1998 | Lepper, Jr. et al. |
| 5,482,036 A | 1/1996 | Diab et al. | 5,743,263 A | 4/1998 | Baker, Jr. |
| 5,485,847 A | 1/1996 | Baker, Jr. | 5,746,206 A | 5/1998 | Mannheimer |
| 5,490,505 A | 2/1996 | Diab et al. | 5,746,697 A | 5/1998 | Swedlow et al. |
| 5,490,523 A | 2/1996 | Isaacson et al. | 5,752,914 A | 5/1998 | DeLonzor et al. |
| 5,491,299 A | 2/1996 | Naylor et al. | 5,755,226 A | 5/1998 | Carim et al. |
| 5,494,032 A | 2/1996 | Robinson et al. | 5,758,644 A | 6/1998 | Diab et al. |
| 5,494,043 A | 2/1996 | O'Sullivan et al. | 5,760,910 A | 6/1998 | Lepper, Jr. et al. |
| 5,497,771 A | 3/1996 | Rosenheimer | 5,766,125 A | 6/1998 | Aoyagi et al. |
| 5,499,627 A | 3/1996 | Steuer et al. | 5,766,127 A | 6/1998 | Pologe et al. |
| 5,503,148 A | 4/1996 | Pologe et al. | 5,769,785 A | 6/1998 | Diab et al. |
| 5,505,199 A | 4/1996 | Kim | 5,772,587 A | 6/1998 | Gratton et al. |
| 5,507,286 A | 4/1996 | Solenberger | 5,774,213 A | 6/1998 | Trebino et al. |
| 5,511,546 A | 4/1996 | Hon | 5,776,058 A | 7/1998 | Levinson et al. |
| 5,517,988 A | 5/1996 | Gerhard | 5,776,059 A | 7/1998 | Kaestle |
| 5,520,177 A | 5/1996 | Ogawa et al. | 5,779,630 A | 7/1998 | Fein et al. |
| 5,521,851 A | 5/1996 | Wei et al. | 5,779,631 A | 7/1998 | Chance |
| 5,522,388 A | 6/1996 | Ishikawa et al. | 5,782,237 A | 7/1998 | Casciani et al. |
| 5,524,617 A | 6/1996 | Mannheimer | 5,782,756 A | 7/1998 | Mannheimer |
| 5,529,064 A | 6/1996 | Rall et al. | 5,782,757 A | 7/1998 | Diab et al. |
| 5,533,507 A | 7/1996 | Potratz et al. | 5,782,758 A | 7/1998 | Ausec et al. |
| 5,551,423 A | 9/1996 | Sugiura | 5,786,592 A | 7/1998 | Hök |
| 5,551,424 A | 9/1996 | Morrison et al. | 5,788,634 A | 8/1998 | Suda et al. |
| 5,553,614 A | 9/1996 | Chance | 5,790,729 A | 8/1998 | Pologe et al. |
| 5,553,615 A | 9/1996 | Carim et al. | 5,792,052 A | 8/1998 | Isaacson et al. |
| 5,555,882 A | 9/1996 | Richardson et al. | 5,795,292 A | 8/1998 | Lewis et al. |
| 5,558,096 A | 9/1996 | Palatnik | 5,797,841 A | 8/1998 | DeLonzor et al. |
| 5,560,355 A | 10/1996 | Merchant et al. | 5,800,348 A | 9/1998 | Kaestle |
| 5,564,417 A | 10/1996 | Chance | 5,800,349 A | 9/1998 | Isaacson et al. |
| 5,575,284 A | 11/1996 | Athan et al. | 5,803,910 A | 9/1998 | Potratz |
| 5,575,285 A | 11/1996 | Takanashi et al. | 5,807,246 A | 9/1998 | Sakaguchi et al. |
| 5,577,500 A | 11/1996 | Potratz | 5,807,247 A | 9/1998 | Merchant et al. |
| 5,582,169 A | 12/1996 | Oda et al. | 5,807,248 A | 9/1998 | Mills |
| 5,584,296 A | 12/1996 | Cui et al. | 5,810,723 A | 9/1998 | Aldrich |
| 5,588,425 A | 12/1996 | Sackner et al. | 5,810,724 A | 9/1998 | Gronvall |
| 5,588,427 A | 12/1996 | Tien | 5,813,980 A | 9/1998 | Levinson et al. |
| 5,590,652 A | 1/1997 | Inai | 5,817,008 A | 10/1998 | Rafert et al. |
| 5,595,176 A | 1/1997 | Yamaura | 5,817,009 A | 10/1998 | Rosenheimer et al. |
| 5,596,986 A | 1/1997 | Goldfarb | 5,817,010 A | 10/1998 | Hibl |
| 5,611,337 A | 3/1997 | Bukta | 5,818,985 A | 10/1998 | Merchant et al. |
| 5,617,852 A | 4/1997 | MacGregor | 5,820,550 A | 10/1998 | Polson et al. |

| Patent | Date | Inventor |
|---|---|---|
| 5,823,950 A | 10/1998 | Diab et al. |
| 5,823,952 A | 10/1998 | Levinson et al. |
| 5,827,179 A | 10/1998 | Lichter et al. |
| 5,827,182 A | 10/1998 | Raley et al. |
| 5,829,439 A | 11/1998 | Yokosawa et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,957,840 A | 9/1999 | Terasawa et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,120 A | 11/1999 | Groner et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,055,447 A | 4/2000 | Weil |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,829 A | 6/2000 | Uchida |
| 6,078,833 A | 6/2000 | Hueber |
| 6,081,735 A | 6/2000 | Diab et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,104,939 A | 8/2000 | Groner |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,151,107 A | 11/2000 | Schöllerman et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,159,147 A | 12/2000 | Lichter |
| 6,163,175 A | 12/2000 | Larsen et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,179,159 B1 | 1/2001 | Gurley |
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grinblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |

| Patent | Date | Name |
|---|---|---|
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B2 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |

| Patent | Date | Inventor |
|---|---|---|
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 * | 1/2006 | Fine et al. ........... 600/335 |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boas et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,112,175 B2 | 9/2006 | Gopinathan et al. |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Kenagy et al. |
| 7,142,901 B2 | 11/2006 | Kiani et al. |
| 7,162,288 B2 | 1/2007 | Nordstrom et al. |
| 7,164,938 B2 | 1/2007 | Geddes et al. |
| 7,190,986 B1 | 3/2007 | Hannula et al. |
| 7,190,987 B2 | 3/2007 | Lindekugel et al. |
| 7,198,778 B2 | 4/2007 | Achilefu et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,881 B2 | 6/2007 | Schmitt et al. |
| 7,245,953 B1 | 7/2007 | Parker |
| 7,248,910 B2 | 7/2007 | Li et al. |
| 7,254,433 B2 | 8/2007 | Diab et al. |
| 7,254,434 B2 | 8/2007 | Schulz et al. |
| 7,257,438 B2 | 8/2007 | Kinast |
| 7,263,396 B2 | 8/2007 | Chen et al. |
| 7,272,425 B2 | 9/2007 | Al-Ali |
| 7,280,858 B2 | 10/2007 | Al-Ali et al. |
| 7,292,150 B2 | 11/2007 | Shaw |
| 7,295,866 B2 | 11/2007 | Al-Ali |
| 7,305,262 B2 | 12/2007 | Brodnick et al. |
| 7,315,753 B2 | 1/2008 | Baker, Jr. et al. |
| 7,341,559 B2 | 3/2008 | Schulz et al. |
| 7,341,560 B2 | 3/2008 | Henderson et al. |
| 7,359,741 B2 | 4/2008 | Sarussi et al. |
| 7,359,742 B2 | 4/2008 | Maser et al. |
| 7,412,272 B2 | 8/2008 | Medina et al. |
| 7,433,726 B2 | 10/2008 | Perkins |
| 7,435,222 B2 | 10/2008 | Gopinathan et al. |
| 2002/0016537 A1 | 2/2002 | Muz et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |

| | | |
|---|---|---|
| 2002/0072681 A1 | 6/2002 | Schnall |
| 2002/0103423 A1 | 8/2002 | Chin et al. |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0151775 A1* | 10/2002 | Kondo .................. 600/344 |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0109775 A1* | 6/2003 | O'Neil et al. ............. 600/323 |
| 2003/0171662 A1 | 9/2003 | O'Connor et al. |
| 2003/0181799 A1 | 9/2003 | Lindekugel et al. |
| 2003/0187337 A1 | 10/2003 | Tarassenko et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2004/0006261 A1 | 1/2004 | Swedlow et al. |
| 2004/0024326 A1 | 2/2004 | Yeo et al. |
| 2004/0039272 A1 | 2/2004 | Abdul-Hafiz et al. |
| 2004/0039273 A1 | 2/2004 | Terry |
| 2004/0054291 A1 | 3/2004 | Schulz et al. |
| 2004/0068164 A1 | 4/2004 | Diab et al. |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0117891 A1 | 6/2004 | Hannula et al. |
| 2004/0122302 A1 | 6/2004 | Mason et al. |
| 2004/0133088 A1 | 7/2004 | Al-Ali |
| 2004/0143172 A1 | 7/2004 | Fudge et al. |
| 2004/0147821 A1 | 7/2004 | Al-Ali et al. |
| 2004/0147824 A1 | 7/2004 | Diab et al. |
| 2004/0158134 A1 | 8/2004 | Diab et al. |
| 2004/0162472 A1 | 8/2004 | Berson et al. |
| 2004/0167381 A1 | 8/2004 | Lichter |
| 2004/0186358 A1 | 9/2004 | Chernow et al. |
| 2004/0199063 A1 | 10/2004 | O'Neil et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215085 A1 | 10/2004 | Schnall |
| 2004/0236196 A1 | 11/2004 | Diab et al. |
| 2004/0257557 A1 | 12/2004 | Block |
| 2004/0260161 A1 | 12/2004 | Melker et al. |
| 2005/0004479 A1 | 1/2005 | Townsend et al. |
| 2005/0014999 A1 | 1/2005 | Rahe-Meyer |
| 2005/0020887 A1 | 1/2005 | Goldberg |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0049471 A1 | 3/2005 | Aceti et al. |
| 2005/0059869 A1 | 3/2005 | Scharf et al. |
| 2005/0070773 A1 | 3/2005 | Chin |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |
| 2005/0119538 A1 | 6/2005 | Jeon et al. |
| 2005/0163412 A1 | 7/2005 | Glebov et al. |
| 2005/0197548 A1 | 9/2005 | Dietiker |
| 2005/0228248 A1 | 10/2005 | Dietiker |
| 2005/0228300 A1 | 10/2005 | Jaime et al. |
| 2005/0256386 A1 | 11/2005 | Chan |
| 2005/0272986 A1 | 12/2005 | Smith |
| 2005/0277819 A1 | 12/2005 | Kiani et al. |
| 2005/0283082 A1 | 12/2005 | Geddes et al. |
| 2006/0020179 A1 | 1/2006 | Anderson |
| 2006/0030764 A1 | 2/2006 | Porges |
| 2006/0036136 A1 | 2/2006 | Shaw |
| 2006/0058594 A1 | 3/2006 | Ishizuka et al. |
| 2006/0058690 A1 | 3/2006 | Bartnik |
| 2006/0064024 A1 | 3/2006 | Schnall |
| 2006/0069319 A1 | 3/2006 | Elhag et al. |
| 2006/0074280 A1 | 4/2006 | Martis |
| 2006/0079794 A1 | 4/2006 | Liu et al. |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |
| 2006/0129039 A1 | 6/2006 | Lindner |
| 2006/0149149 A1 | 7/2006 | Schmid |
| 2006/0155198 A1 | 7/2006 | Schmid |
| 2006/0173257 A1 | 8/2006 | Nagai |
| 2006/0200018 A1 | 9/2006 | Al-Ali |
| 2006/0253010 A1 | 11/2006 | Brady et al. |
| 2006/0276700 A1 | 12/2006 | O'Neil et al. |
| 2007/0021659 A1 | 1/2007 | Delonzor et al. |
| 2007/0021660 A1 | 1/2007 | Delonzor et al. |
| 2007/0021662 A1 | 1/2007 | Delonzor et al. |
| 2007/0027376 A1 | 2/2007 | Todokoro et al. |
| 2007/0027378 A1 | 2/2007 | Delonzor et al. |
| 2007/0027379 A1 | 2/2007 | Delonzor et al. |
| 2007/0027380 A1 | 2/2007 | Delonzar et al. |
| 2007/0032707 A1 | 2/2007 | Coakley et al. |
| 2007/0032708 A1 | 2/2007 | Eghbal et al. |
| 2007/0032709 A1 | 2/2007 | Coakley et al. |
| 2007/0032710 A1 | 2/2007 | Raridan et al. |
| 2007/0032711 A1 | 2/2007 | Coakley et al. |
| 2007/0032712 A1 | 2/2007 | Raridan et al. |
| 2007/0032715 A1 | 2/2007 | Eghbal et al. |
| 2007/0032716 A1 | 2/2007 | Raridan et al. |
| 2007/0038050 A1 | 2/2007 | Sarussi |
| 2007/0060808 A1 | 3/2007 | Hoarau |
| 2007/0073117 A1 | 3/2007 | Raridan |
| 2007/0073121 A1 | 3/2007 | Hoarau et al. |
| 2007/0073122 A1 | 3/2007 | Hoarau |
| 2007/0073123 A1 | 3/2007 | Raridan |
| 2007/0073125 A1 | 3/2007 | Hoarau et al. |
| 2007/0073126 A1 | 3/2007 | Raridan |
| 2007/0078315 A1 | 4/2007 | Kling et al. |
| 2007/0078316 A1 | 4/2007 | Hoarau et al. |
| 2007/0106132 A1 | 5/2007 | Elhag et al. |
| 2007/0219440 A1 | 9/2007 | Hannula et al. |
| 2007/0260129 A1 | 11/2007 | Chin |
| 2007/0260130 A1 | 11/2007 | Chin |
| 2007/0260131 A1 | 11/2007 | Chin |
| 2007/0299328 A1 | 12/2007 | Chin et al. |
| 2008/0009691 A1 | 1/2008 | Parker et al. |
| 2008/2000786 | 8/2008 | Berndsen |
| 2008/0262328 A1 | 10/2008 | Adams |

FOREIGN PATENT DOCUMENTS

| | | |
|---|---|---|
| DE | 3405444 | 8/1985 |
| DE | 3516338 | 11/1986 |
| DE | 37 03 458 | 8/1988 |
| DE | 3938759 | 5/1991 |
| DE | 4210102 | 9/1993 |
| DE | 4423597 | 8/1995 |
| DE | 19632361 | 2/1997 |
| DE | 69123448 | 5/1997 |
| DE | 19703220 | 7/1997 |
| DE | 19640807 | 9/1997 |
| DE | 19647877 | 4/1998 |
| DE | 10030862 | 1/2002 |
| DE | 20318882 | 4/2004 |
| EP | 0127947 | 5/1984 |
| EP | 00194105 | 9/1986 |
| EP | 00204459 | 12/1986 |
| EP | 204459 | 12/1986 |
| EP | 0 262 779 | 4/1988 |
| EP | 0315040 | 10/1988 |
| EP | 0314331 | 5/1989 |
| EP | 00352923 | 1/1990 |
| EP | 0 360 977 | 4/1990 |
| EP | 00430340 | 6/1991 |
| EP | 430340 | 6/1991 |
| EP | 0435 500 | 7/1991 |
| EP | 0572684 | 5/1992 |

| | | | | | | |
|---|---|---|---|---|---|---|
| EP | 00497021 | 8/1992 | | JP | 22224088 | 8/2002 |
| EP | 0529412 | 8/1992 | | JP | 22282242 | 10/2002 |
| EP | 0531631 | 9/1992 | | JP | 23153881 | 5/2003 |
| EP | 0566354 | 4/1993 | | JP | 23153882 | 5/2003 |
| EP | 0587009 | 8/1993 | | JP | 23169791 | 6/2003 |
| EP | 00630203 | 9/1993 | | JP | 23194714 | 7/2003 |
| EP | 0 572 684 | 12/1993 | | JP | 23210438 | 7/2003 |
| EP | 00615723 | 9/1994 | | JP | 23275192 | 9/2003 |
| EP | 00702931 | 3/1996 | | JP | 23339678 | 12/2003 |
| EP | 00724860 | 8/1996 | | JP | 24008572 | 1/2004 |
| EP | 724860 | 8/1996 | | JP | 24089546 | 3/2004 |
| EP | 00793942 | 9/1997 | | JP | 24113353 | 4/2004 |
| EP | 0 864 293 | 9/1998 | | JP | 24135854 | 5/2004 |
| EP | 01006863 | 10/1998 | | JP | 24148069 | 5/2004 |
| EP | 01006864 | 10/1998 | | JP | 24148070 | 5/2004 |
| EP | 0875199 | 11/1998 | | JP | 24159810 | 6/2004 |
| EP | 00998214 | 12/1998 | | JP | 24166775 | 6/2004 |
| EP | 0 898 933 | 3/1999 | | JP | 24194908 | 7/2004 |
| EP | 0 898 933 A2 | 3/1999 | | JP | 24202190 | 7/2004 |
| EP | 01332713 | 8/2003 | | JP | 24248819 | 9/2004 |
| EP | 01469773 | 8/2003 | | JP | 24248820 | 9/2004 |
| EP | 1502529 | 7/2004 | | JP | 24261364 | 9/2004 |
| EP | 01491135 | 12/2004 | | JP | 24290412 | 10/2004 |
| EP | 1491135 | 12/2004 | | JP | 24290544 | 10/2004 |
| EP | 1807001 | 7/2007 | | JP | 24290545 | 10/2004 |
| FR | 2685865 | 1/1992 | | JP | 24329406 | 11/2004 |
| GB | 2 259 545 | 3/1993 | | JP | 24329607 | 11/2004 |
| JP | 63275325 | 11/1988 | | JP | 24329928 | 11/2004 |
| JP | 2013450 | 1/1990 | | JP | 24337605 | 12/2004 |
| JP | 2111343 | 4/1990 | | JP | 24344367 | 12/2004 |
| JP | 02 191434 | 7/1990 | | JP | 24351107 | 12/2004 |
| JP | 2237544 | 9/1990 | | JP | 25034472 | 2/2005 |
| JP | 03 173536 | 7/1991 | | JP | 25110816 | 4/2005 |
| JP | 3170866 | 7/1991 | | JP | 25125106 | 5/2005 |
| JP | 3245042 | 10/1991 | | JP | 25168600 | 6/2005 |
| JP | 4174648 | 6/1992 | | JP | 26122458 | 5/2006 |
| JP | 4191642 | 7/1992 | | JP | 26122693 | 5/2006 |
| JP | 4332536 | 11/1992 | | WO | WO 98/09566 | 10/1989 |
| JP | 3124073 | 3/1993 | | WO | WO 90/01293 | 2/1990 |
| JP | 5049624 | 3/1993 | | WO | WO9001293 | 2/1990 |
| JP | 5049625 | 3/1993 | | WO | WO 90/04352 | 5/1990 |
| JP | 3115374 | 4/1993 | | WO | WO 91/01678 | 2/1991 |
| JP | 05 200031 | 8/1993 | | WO | WO 91/11137 | 8/1991 |
| JP | 2005/200031 | 8/1993 | | WO | WO 92/00513 | 1/1992 |
| JP | 5212016 | 8/1993 | | WO | WO 92/21281 | 12/1992 |
| JP | 06 014906 | 1/1994 | | WO | WO 93/09711 | 5/1993 |
| JP | 06014906 | 1/1994 | | WO | WO 93/13706 | 7/1993 |
| JP | 6016774 | 3/1994 | | WO | WO 93/16629 | 9/1993 |
| JP | 3116255 | 4/1994 | | WO | WO 94/03102 | 2/1994 |
| JP | 6029504 | 4/1994 | | WO | WO 94/23643 | 10/1994 |
| JP | 6098881 | 4/1994 | | WO | WO 95/02358 | 1/1995 |
| JP | 06 154177 | 6/1994 | | WO | WO 95/12349 | 5/1995 |
| JP | 6269430 | 9/1994 | | WO | WO 95/16970 | 6/1995 |
| JP | 6285048 | 10/1994 | | WO | WO 96/13208 | 5/1996 |
| JP | 7001273 | 1/1995 | | WO | WO9616591 | 6/1996 |
| JP | 7124138 | 5/1995 | | WO | WO 96/39927 | 12/1996 |
| JP | 7136150 | 5/1995 | | WO | WO 97/36536 | 10/1997 |
| JP | 3116259 | 6/1995 | | WO | WO 97/36538 | 10/1997 |
| JP | 3116260 | 6/1995 | | WO | WO 97/49330 | 12/1997 |
| JP | 7155311 | 6/1995 | | WO | WO 98/17174 | 4/1998 |
| JP | 7155313 | 6/1995 | | WO | WO 98/18382 | 5/1998 |
| JP | 3238813 | 7/1995 | | WO | WO 98/43071 | 10/1998 |
| JP | 7171139 | 7/1995 | | WO | WO 98/51212 | 11/1998 |
| JP | 3134144 | 9/1995 | | WO | WO 98/57577 | 12/1998 |
| JP | 7236625 | 9/1995 | | WO | WO 98/57577 A1 | 12/1998 |
| JP | 7246191 | 9/1995 | | WO | WO 99/00053 | 1/1999 |
| JP | 8256996 | 10/1996 | | WO | WO 99/32030 | 7/1999 |
| JP | 9192120 | 7/1997 | | WO | WO 99/47039 | 9/1999 |
| JP | 10216113 | 8/1998 | | WO | WO 99/63884 | 12/1999 |
| JP | 10216114 | 8/1998 | | WO | WO 00/21438 | 4/2000 |
| JP | 10216115 | 8/1998 | | WO | WO 00/28888 | 5/2000 |
| JP | 10337282 | 12/1998 | | WO | WO 00/59374 | 10/2000 |
| JP | 11019074 | 1/1999 | | WO | WO 01/13790 | 3/2001 |
| JP | 11155841 | 6/1999 | | WO | WO 01/16577 | 3/2001 |
| JP | 11 188019 | 7/1999 | | WO | WO 01/17421 | 3/2001 |
| JP | 11244268 | 9/1999 | | WO | WO 01/47426 | 3/2001 |
| JP | 20107157 | 4/2000 | | WO | WO 01/40776 | 6/2001 |
| JP | 20237170 | 9/2000 | | WO | WO 01/67946 | 9/2001 |
| JP | 21245871 | 9/2001 | | WO | WO 01/76461 | 10/2001 |

| | | |
|---|---|---|
| WO | WO 02/14793 | 2/2002 |
| WO | WO 02/35999 | 5/2002 |
| WO | WO 02/062213 | 8/2002 |
| WO | WO 02/074162 A | 9/2002 |
| WO | WO 02/85202 | 10/2002 |
| WO | WO 03/000125 | 1/2003 |
| WO | WO 03/001180 A2 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 2004/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO2005053530 | 6/2005 |
| WO | WO 2005/065540 | 7/2005 |
| WO | WO2006064399 | 6/2006 |
| WO | WO2006110488 | 10/2006 |

OTHER PUBLICATIONS

Zahar, N., et al.; "Automatic Feedback Control of Oxygen Therapy Using Pulse Oximetry, *Annual International Conference of the IEEE Engineering in Medicine and Biology Society*," vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biologo Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the $22^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the $22^{nd}$ Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing* vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 451 5, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, vol. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; "Multiple diagnosis based on Photoplethysmography: hematocrib, SpO2, pulse and respiration," *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo* (*Aritificial Respiration*), vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2$ /$SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2$ /$SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

Sokwoo Rhee et al. "Artifact-Resistant Power-Efficient Design of Finger-Ring Plethysmographic Sensors," IEEE Transactions on Biomedical Engineering, vol. 48, No. 7, Jul. 2001, pp. 795-805.

H. Harry Asada et al. "A New Ring Sensor Design for Improved Motion Artifact Reduction without Circulatory Interference," Progress Report No. 3-3, Oct. 1, 2001-Mar. 31, 2002, MIT Home Automation and Healthcare Consortium, pp. 1-45.

* cited by examiner

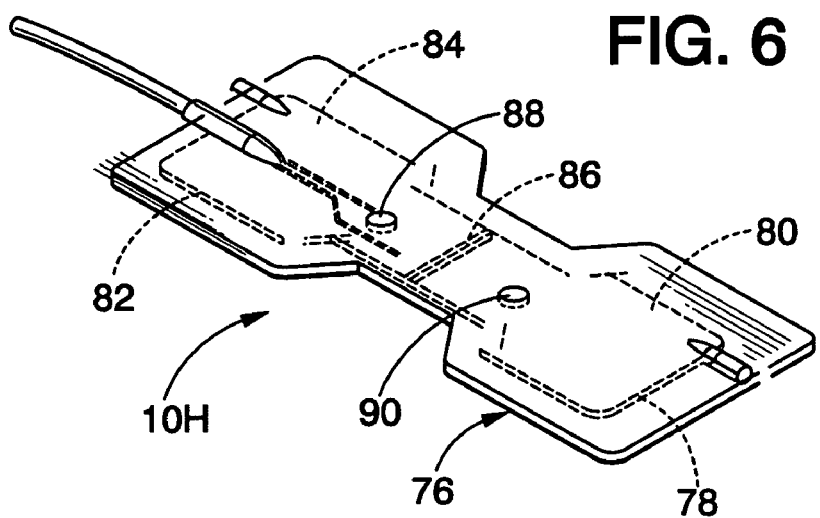
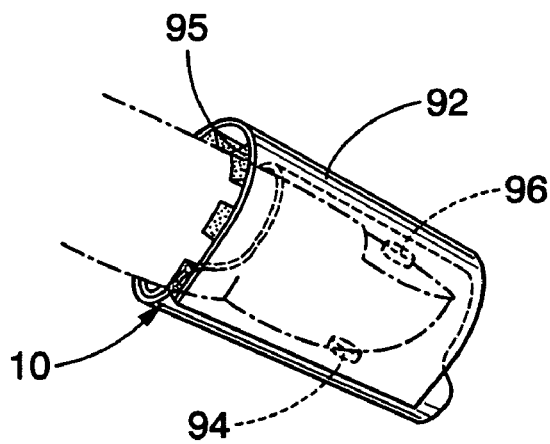
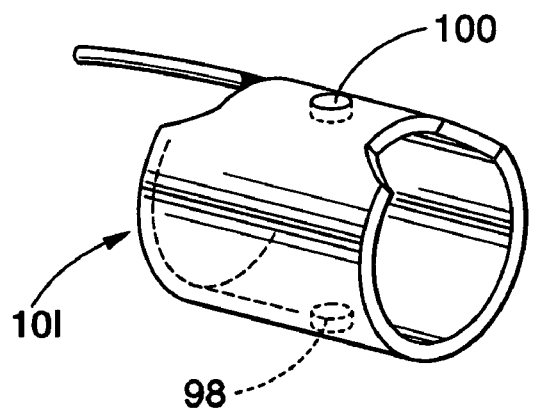

FIG. 11A
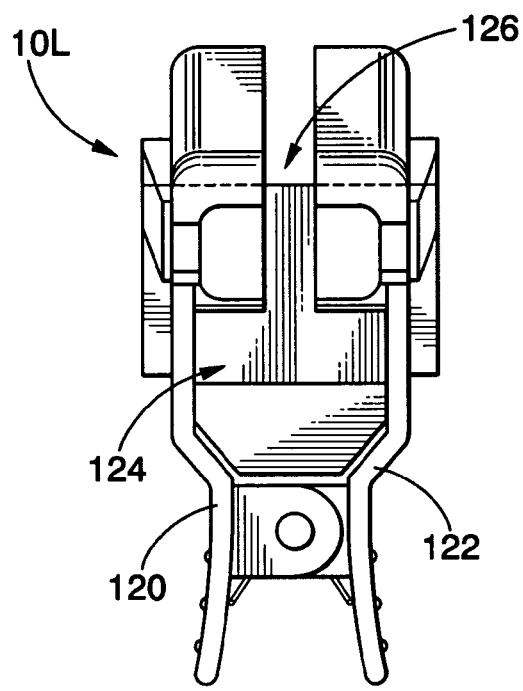
FIG. 11B
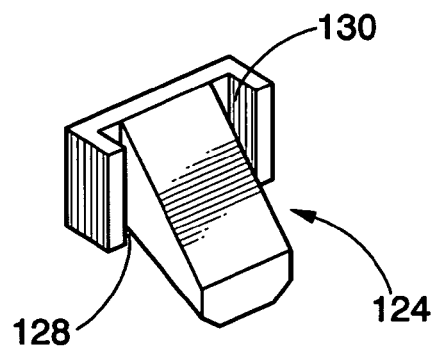
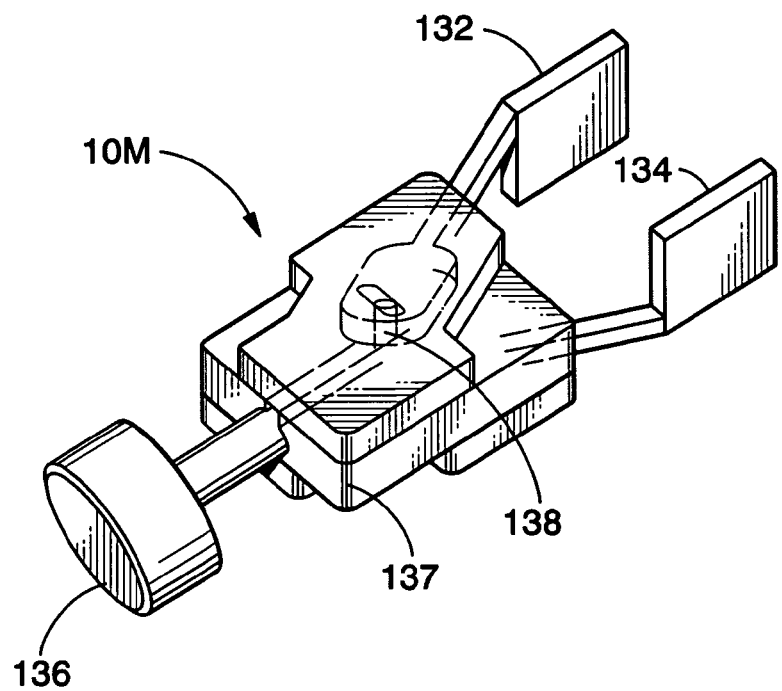
FIG. 12

MEDICAL SENSOR FOR REDUCING MOTION ARTIFACTS AND TECHNIQUE FOR USING THE SAME

CROSS-REFERENCE TO RELATED APPLICATION

This application is a continuation of U.S. application Ser. No. 11/241,375 filed Sep. 29, 2005, the disclosure of which is hereby incorporated by reference in its entirety.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits electromagnetic radiation, such as light, through a patient's tissue and that photoelectrically detects the absorption and scattering of the transmitted light in such tissue. One or more of the above physiological characteristics may then be calculated based upon the amount of light absorbed and scattered. More specifically, the light passed through the tissue is typically selected to be of one or more wavelengths that may be absorbed and scattered by the blood in an amount correlative to the amount of the blood constituent present in the tissue. The measured amount of light absorbed and scattered may then be used to estimate the amount of blood constituent in the tissue using various algorithms.

Pulse oximetry readings measure the pulsatile, dynamic changes in amount and type of blood constituents in tissue. Other events besides the pulsing of arterial blood may lead to modulation of the light path, direction, and the amount of light detected by the sensor, creating error in these measurements. Pulse oximetry is sensitive to movement, and various types of motion may cause artifacts that may obscure the blood constituent signal. For example, motion artifacts may be caused by moving a sensor in relation to the tissue, by increasing or decreasing the physical distance between emitters and detectors in a sensor, by changing the direction of emitters or detectors with respect to tissue or each other, by changing the angles of incidence and interfaces probed by the light, by directing the optical path through different amounts or types of tissue, or by expanding, compressing or otherwise altering tissue near a sensor. In the emergency room, critical care, intensive care, and trauma center settings, where pulse oximetry is commonly used for patient monitoring, the wide variety of sources of motion artifacts includes moving of a patient or the sensor by healthcare workers, physical motion of an unanaesthetised or ambulatory patient, shivering, seizures, agitation, response to pain and loss of neural control. These motions oftentimes have similar frequency content to the pulse, and may lead to similar or even larger optical modulations than the pulse.

Two categories of pulse oximetry sensors in common use may be classified by their pattern of use: the disposable and the reusable sensor. Disposable sensors are typically flexible bandage-type structures that may be attached to the patient with adhesive materials, providing a contact between the patient's skin and the sensor components. Disposable sensors have multiple advantages, including ease of conformation to the patient. The flexible nature of disposable sensors further renders them susceptible to motion artifacts caused by mechanical deformation of the sensor, which changes the amount of light detected. Reusable sensors, often semi-rigid or rigid clip-type devices, are also vulnerable to motion artifacts, such as artifacts caused by partial opening of the clip in response to patient motion. Both categories of sensors may have modulations of detected light induced by the physical motion of the sensor components with respect to each other and the tissue.

Motion artifacts may sometimes be addressed by signal processing and filtering to mitigate the effects of motion after the motion has occurred. However, it would be desirable to provide a sensor that reduces the occurrence of movement that may lead to motion artifacts.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a sensor that includes a sensor body, and an emitter and a detector disposed on the sensor body. The sensor body is adapted to hold the emitter and detector at a substantially fixed optical distance relative to one another when the sensor is applied to a patient.

There is also provided a pulse oximetry system that includes a pulse oximetry monitor and a pulse oximetry sensor adapted to be operatively coupled to the monitor. The sensor includes a sensor body, and an emitter and a detector disposed on the sensor body. The sensor body is adapted to hold the emitter and detector at a substantially fixed optical distance relative to one another when the sensor is applied to a patient.

There is also provided a method of operating a sensor that includes fixing the optical distance between an emitter and a detector relative to one another, whereby the emitter and the detector are disposed on a sensor body.

There is also provided a method of manufacturing a sensor that includes providing a sensor body on which an emitter and a detector are disposed, whereby the sensor body is adapted to hold the emitter and the detector at a fixed optical distance.

BRIEF DESCRIPTION OF THE DRAWINGS

Advantages of the invention may become apparent upon reading the following detailed description and upon reference to the drawings in which:

FIG. 6 illustrates a perspective view of an exemplary bandage-style pulse oximetry sensor with two fluid-filled chambers separated by a breakable barrier;

FIG. 7 illustrates a perspective view of an exemplary pulse oximetry sensor according to the present invention with a removable rigid sleeve;

FIG. 8A illustrates a perspective view of an exemplary annular pulse oximetry sensor according to the present invention;

FIG. 11A illustrates a cross-sectional view of an exemplary clip-style pulse oximetry sensor with a removable spacer according to the present invention;

FIG. 11B is a perspective view of the removable spacer of FIG. 11A;

FIG. 12 illustrates a perspective view of an exemplary clip-style pulse oximetry sensor in which the two portions of the clip are adjusted with a sliding pin.

DETAILED DESCRIPTION OF SPECIFIC EMBODIMENTS

Figure 1:
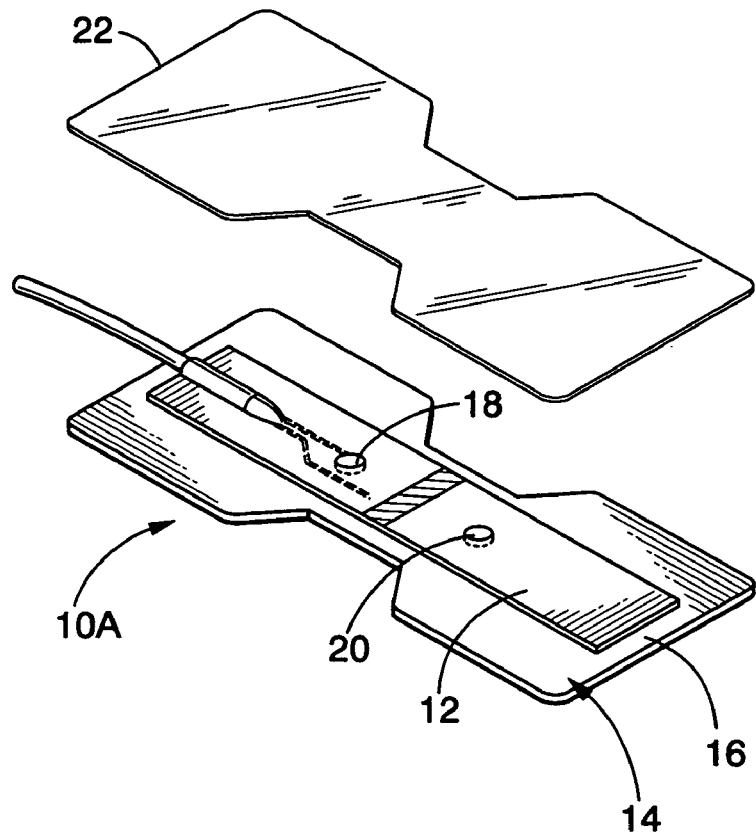
FIG. 1 illustrates a perspective view of an exemplary bandage-style pulse oximetry sensor with a stiffening member on the tissue-contacting side of the sensor body.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, sensors for pulse oximetry or other applications utilizing spectrophotometry are provided that reduce motion artifacts by fixing the optical distance between an emitter and a detector when the sensor is applied to a patient. For example, in one embodiment, a conformable sensor is provided that has a stiffening member adapted to hold the emitter and detector at a fixed optical distance when the sensor is applied to a patient. In another embodiment, an annular or partially annular sensor is provided that maintains a fixed optical distance between an emitter and a detector when the sensor is applied to a patient's digit. Further, in an additional embodiment, a clip-style sensor is provided that holds the emitter and detector at a fixed optical distance.

Motion artifacts in pulse oximetry are often generated by the movement of the pulse oximetry sensor relative to the optically probed tissue, which is typically caused by patient movement. Because pulse oximetry is often used in settings where it is difficult to prevent patient motion, it is desirable to provide a mechanism for reducing the effects of motion on the pulse oximetry measurement. Generally, sensors are vulnerable to motion artifacts when the optical distance between a sensor's emitter and detector varies due to an undesired mechanical change in the conformation of the sensor while in use.

A change in optical distance may include any change in position or geometry of the emitter and/or the detector relative to the tissue or relative to each other. More specifically, a change in optical distance may involve a change in the path length, a change in the angle of the emitter or detector relative to one another, and/or a change in the angle of the emitter or detector relative to the tissue. For example, a tapping or pressing motion by a patient may serve to compress a flexible bandage sensor, decreasing the path length between the emitter and detector. Alternatively, a tapping or pressing motion may partially open a clip-type sensor through pressure on the clip spring, thus increasing the path length between the emitter and detector. For both a bandage and a clip-style sensor, a jerking or flexing motion may separate the emitter and detector, thus increasing the optical path length. Additionally, any of the above motions may twist or bend the sensor, causing the angle of the emitter and/or the detector to change relative to the sensor and each other. As sensors do not typically emit nor detect light omnidirectionally; any motions that lead to variations in angle of sensor components may alter the amount of light detected, and may force detected light through different portions of tissue. In any case, variability in the optical path length due to motion can cause motion artifacts and obscure the desired pulse oximetry signal. Thus, it is desirable that a sensor's emitter and detector are held at a substantially fixed optical distance with respect to one another.

By holding a sensor's emitter and detector at a substantially fixed optical position with respect to one another, the sensors provided herein limit the modulations of detected light that may occur and the resulting measurement errors. These sensors substantially reduce the occurrence of motion artifacts by reducing the change in position of the sensing components of the sensor with respect to each other and the tissue.

Keeping in mind the preceding points, the following exemplary sensor designs are provided as examples of sensors that reduce motion artifacts by maintaining a fixed optical distance between an emitter and a detector of a sensor 10. It should be appreciated that a sensor 10 according to the present teachings may be adapted for use on any digit, and may also be adapted for use on a forehead, earlobe, or other sensor site. For example, a sensor 10 may be a clip-style sensor, appropriate for a patient earlobe or digit. Alternatively, a sensor 10 may be a bandage-style or wrap-style sensor for use on a digit or forehead. Further, it should be appreciated that a sensor 10 may also include adhesives to facilitate securing of the sensing elements to the tissue. In certain embodiments, the adhesives may include an adhesive coating on the tissue-contacting surface of the sensor 10.

In accordance with some embodiments of the present technique, sensors for pulse oximetry or other applications utilizing spectrophotometry are provided having a stiffening member to reduce variability in the optical distance between an emitter and a detector. For example, FIG. 1A illustrates an exemplary transmission-type bandage sensor appropriate for use on a patient digit. As shown in FIG. 1A, a sensor 10A may have a stiffening member 12 that is applied to a conformable sensor body 14. The stiffening member 12 may be applied to a tissue-contacting surface 16, adhesively or otherwise. As the stiffening member 12 may come into contact with a patient's tissue, it may be generally constructed to have no sharp edges in order to avoid patient discomfort. The stiffening member 12 may have windows or other openings (not shown) suitably sized to accommodate an emitter 18 and a detector 20. The stiffening member 12 may applied such that the windows or openings are in-line with the emitter and the detector to allow for normal light emitting and photodetecting function. The sensor 10A may optionally include an optically transparent adhesive layer 22 for affixing the sensor to the digit. The adhesive layer 22 may be generally sized and shaped to cover the tissue-contacting surface 16 of the conformable sensor body 22. When the sensor 10A is applied to a patient's digit, the stiffening member is bent or otherwise shaped to conform to the digit. The sensor 10A is applied such that the emitter 18 and the detector 20 lie on opposing side of the digit. After application of the sensor 10A, the emitter 18 and the detector 20 are substantially resistant to movement relative to one another.

The stiffening member 12 (and stiffening members 36 and 42, below) may be constructed from any suitable material that functions to hold the emitter and the detector of a sensor at a substantially fixed optical distance when the sensor 10A is applied to a patient. For example, a suitable stiffening member 12 may be metal, plastic or polymeric, or cardboard. In certain embodiments, suitable metals include aluminum or brass. The stiffening member 12 may be in the shape of a strip, wire, or mesh that can be easily adapted for use with a conformable sensor body 14. The stiffening member 12 may adapted to be easily bent, shaped, activated, or applied to a conformable sensor body 14 in order to hold an emitter and a detector at a substantially fixed optical distance. The stiffening member 12 may be sized to substantially cover a majority of the tissue-contacting surface 16, or for reasons related to cost or total sensor weight, may be sized to form a strip that is generally in the area surrounding the emitter 18 and the detector 20.

Figure 2:
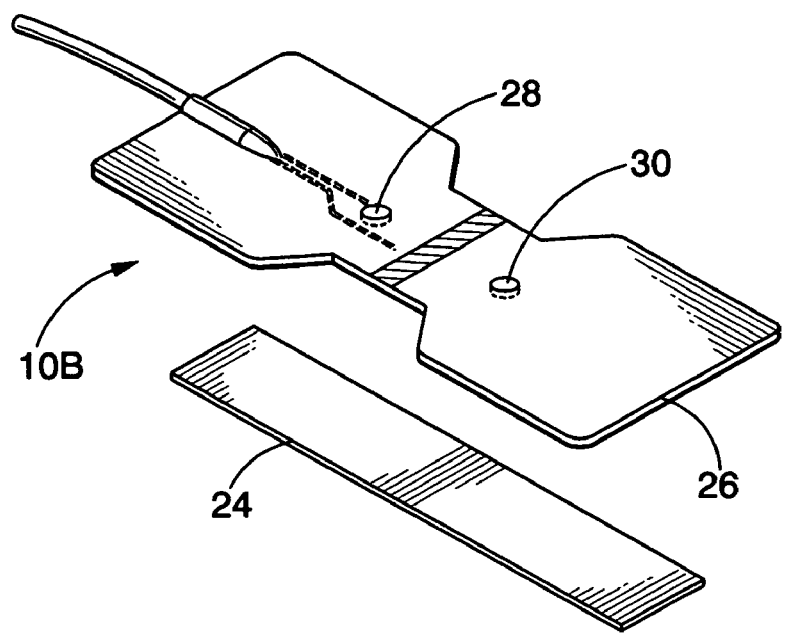
FIG. 2 illustrates a perspective view of an exemplary bandage-style pulse oximetry sensor with a brass stiffening member applied to the surface of the sensor body that does not contact a patient's tissue during normal use.

In certain embodiments, it may be advantageous to apply a stiffening member to a sensor surface that does not contact a patient's tissue during normal use. For example, certain patients may be sensitive to metals, and thus in certain circumstances it may be desirable to limit the amount of skin contact with a metal stiffening member. For those patients, a sensor 10B as shown in FIG. 2 may be appropriate. FIG. 2 shows an embodiment of a sensor 10B in which a brass stiffening member 24 is applied to a surface 26 that does not contact the tissue during normal use of the sensor 10B. The brass stiffening member 24 is applied to the surface 26 along an imaginary axis connecting an emitter 28 and a detector 30. When the sensor 10B is applied to a patient's digit, the brass stiffening member 24 is bent to conform to the digit without coming in contact with the patient's tissue. In an alternate embodiment (not shown), the sensor 10B is adapted to operate in reflectance mode. The emitter 28 and detector 30 are positioned on the sensor body such that they lay side-by-side when applied to a patient's digit.

Figure 3A:
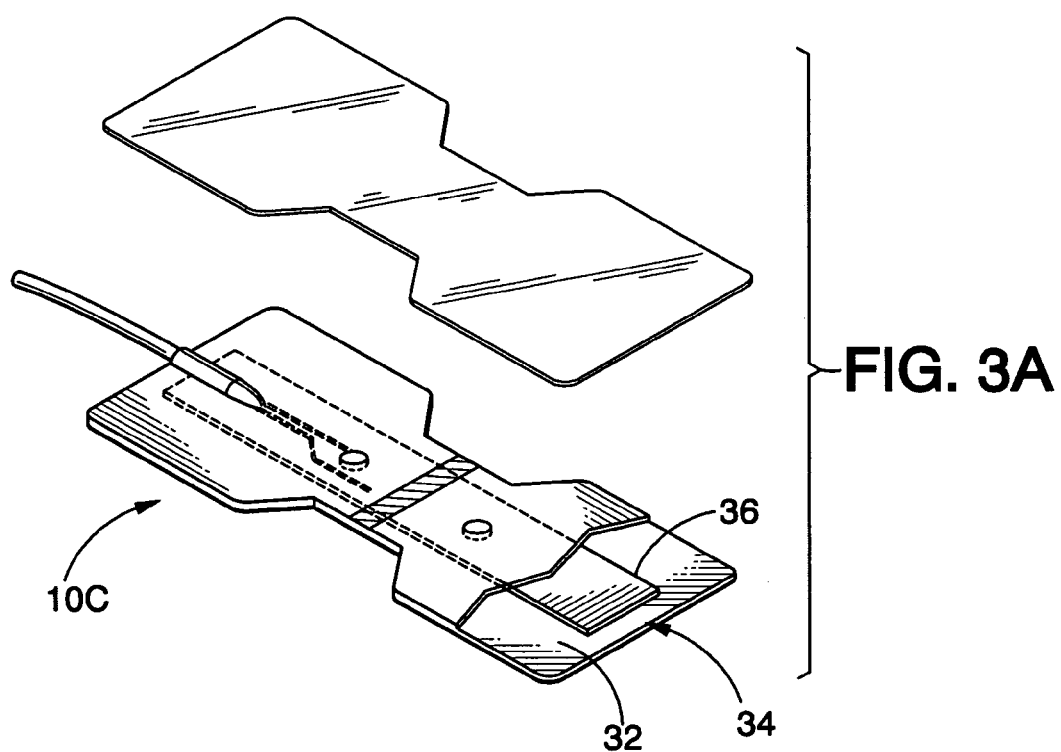
FIG. 3A illustrates a view showing the interior of an exemplary bandage-style pulse oximetry sensor with an embedded stiffening member.
Figure 3B:
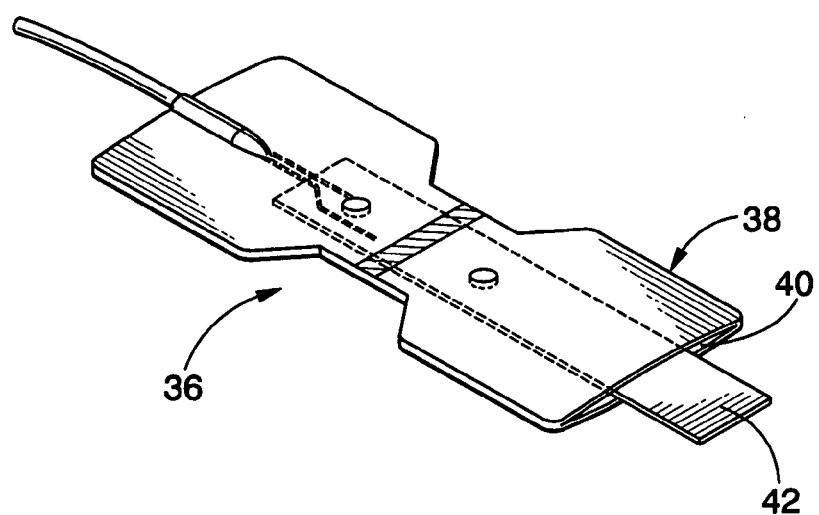
FIG. 3B illustrates a perspective view of an exemplary bandage-style pulse oximetry sensor with an embedded, removable stiffening member.

In certain embodiments, a stiffening member may be integrally constructed with the conformable sensor body, or may be a separate structure. More specifically, in the embodiment shown in FIG. 3A, a sensor 10C has a closed cavity 32 within the conformable sensor body 34 into which a stiffening member 36 may be integrated or embedded. Alternatively, in certain embodiments, it may be advantageous to apply the stiffening member to the sensor at the time of use. FIG. 3B illustrates sensor 10D in which the conformable sensor body 38 has an open cavity 40 that extends along the sensor body to provide an opening into which a removable stiffening member 42 may be manually inserted at the time of application of the sensor 10D to a patient. Before the sensor 10D is discarded after use, the removable stiffening member 42 may be removed and stored for reuse. Having a removable stiffening member 42 that is reusable is not integral to the sensor 10D may decrease sensor weight for shipping and transport, and thus may provide certain cost advantages.

Figure 4A:
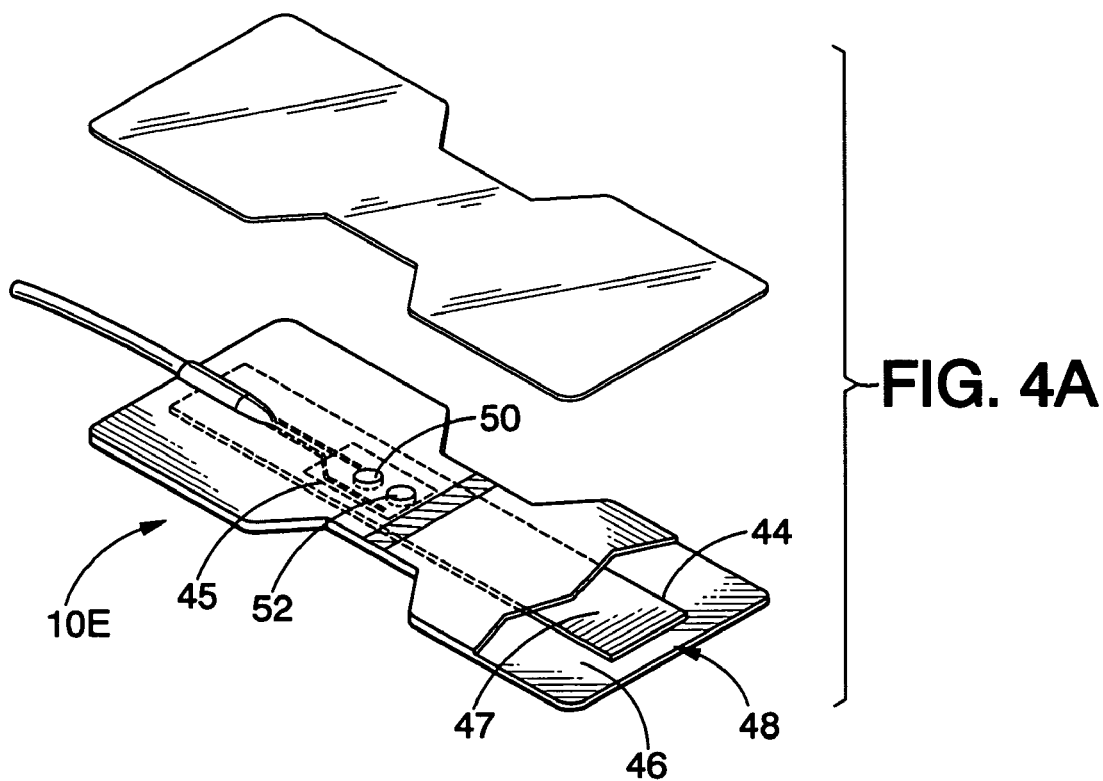
FIG. 4A illustrates a view showing the interior of an exemplary reflectance bandage-style pulse oximetry sensor with an embedded stiffening member including a rigid portion that surrounds the emitter and the detector and a flexible portion.
Figure 4B:
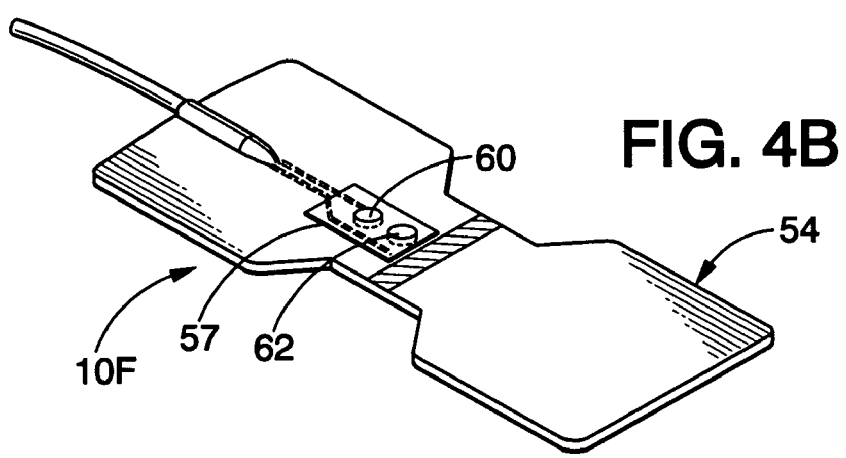
FIG. 4B illustrates a view showing an exemplary reflectance bandage-style pulse oximetry sensor with a stiffening member surrounding the emitter and detector.
Figure 4C:
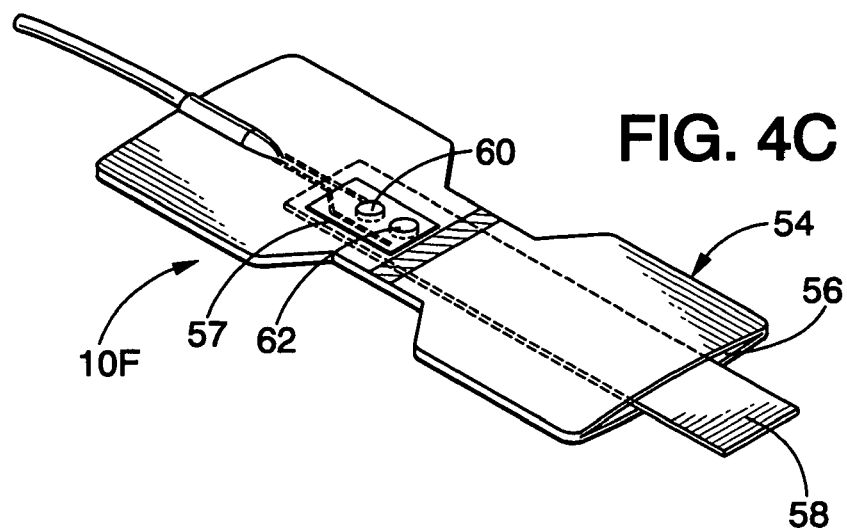
FIG. 4C illustrates a perspective view of an exemplary reflectance bandage-style pulse oximetry sensor with a rigid portion that surrounds the emitter and the detector and an embedded, removable stiffening member that is flexible.

In an alternate embodiment shown in FIG. 4A, a sensor 10E with an embedded stiffening member 44 within a closed cavity 46 in the conformable sensor body 48 may be adapted to operate in reflectance mode, such the emitter 50 and the detector 52 lie side-by-side when the sensor is applied to a patient. The stiffening member 44 includes a rigid portion 45 disposed in the area adjacent to the emitter 50 and the detector 52 and a more flexible portion 47. Thus, when the sensor 10E is applied to a patient, the flexible portion 47 of the stiffening member 44 allows the sensor 10E to be bent around a digit while adding stability to the conformable sensor body 48. The rigid portion 45 surrounding the emitter 50 and the detector 52 may fix the geometry of sensing elements, substantially reducing their ability to move relative to one another. In an alternate embodiment, FIG. 4B illustrates reflectance sensor 10F in which the conformable sensor body 54 includes a rigid portion 57 that surrounds the emitter 60 and the detector 62. The rigid portion may be embedded in the sensor body 54, or may be disposed on the tissue-contacting surface of the sensor body 54. FIG. 4C illustrates an alternate embodiment of the sensor 10F in which the conformable sensor body 54 has an open cavity 56 that extends along the sensor body to provide an opening into which a flexible member 58 may be manually inserted at the time of application of the sensor 10F to a patient. The rigid portion 57 is separate from the removable flexible member 58. Thus, if a healthcare worker feels that additional sensor 10F stability may be advantageous, the flexible member 58 may be inserted into the sensor 10F. When the sensor is applied to the patient, the emitter 60 and the detector 62 lie side-by-side on the same side of the tissue.

Figure 5A:
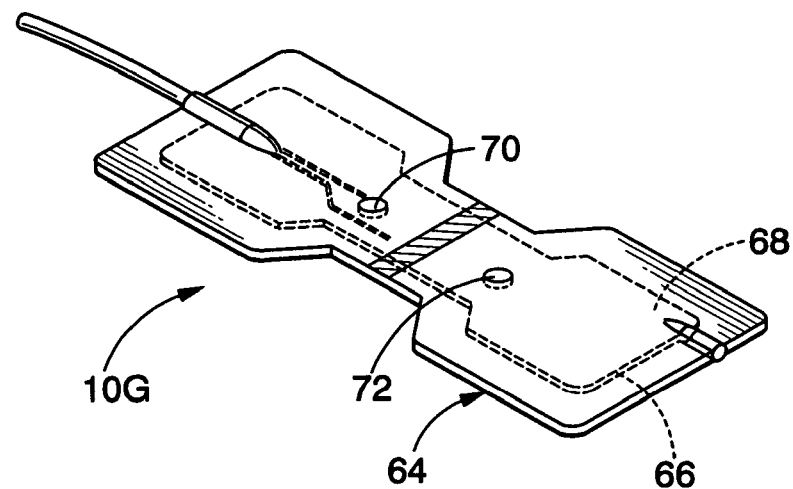
FIG. 5A illustrates a perspective view of an exemplary bandage-style pulse oximetry sensor with a fluid-filled chamber.

A stiffening member need not be solid, but may also be a fluid or other non-solid material that stabilizes the optical distance between an emitter and a detector. In another embodiment, FIG. 5A shows a sensor 10G in which the conformable sensor body 64 contains a bladder 66 that is adapted to hold a fluid 68. The fluid 68 may be a liquid, gel, gas, or any suitable mixture thereof. It is contemplated that the stiffening qualities of a gas or liquid may be realized by achieving a certain pressure in the bladder 66. Generally, it is contemplated that the bladder 66 should be fully inflated or mostly inflated with the fluid 68 to hold the emitter 70 and the detector 72 at a fixed optical distance. In certain embodiments, a liquid or gel may harden after a period of time. The fluid 66 described in the above embodiment may be any suitable fluid that acts to hold an emitter 70 and a detector 72 at a substantially fixed optical distance when the sensor 10G is applied to a patient's digit. In certain embodiments, the fluid may be air or other gases and gas mixtures. In other embodiments, the fluid may be water.

Figure 5B:
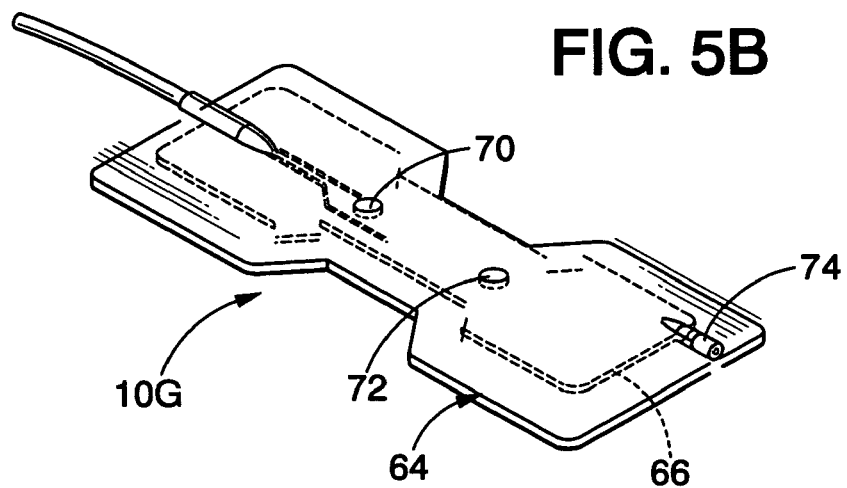
FIG. 5B illustrates a perspective view of the pulse oximetry sensor of FIG. 5A in which the fluid-filled chamber includes a valve.

In certain embodiments, it may be desirable employ a gas or gas mixture for reasons related to cost, manufacturing convenience, and total sensor weight. In FIG. 5B, the sensor 10G is modified to include a valve 74 or another suitable opening or gas injection site. The sensor may be applied to a patient's digit when the valve 74 is in the closed position and the bladder 66 is substantially empty and deflated. After application of the sensor 10G to the digit, the valve 74 is opened to allow air to flow into the bladder 66, which stiffens the sensor 10G to fix the distance between the emitter 70 and the detector 72. In other embodiments, the valve 74 may be a fluid or epoxy injection site.

Another embodiment in which a fluid-containing stiffening member may be activated upon application of the sensor to a patient is illustrated in FIG. 6. FIG. 6 depicts a sensor 10H with a first chamber 78 filled with a first material 80, and second chamber 82 filled with a second material 84. A barrier 86 separates the first chamber 78 and second chamber 82. The barrier 86 is capable of being broken upon applying the sensor 82 to a patient. After the breaking of the barrier 86, the first material 80 and the second material 84 will mix and form a composition that is capable of hardening, thus stabilizing the optical distance between the emitter 88 and detector 90. For example, the first material 80 may be cement or plaster, and the second material 84 may be water. In another embodiment, the first material 80 may be epoxy. In another embodiment, the first material 80 may be one part of a two-part epoxy in which a first part of the epoxy, such as the base, is the first materials 80, and a second part of the epoxy, such as the catalyst or hardener, is the second material 84. Two part epoxies that may be used with a sensor 10H include Loctite® 30680 (available from Henkel, Rocky Hill, Conn.), Blu-Mousse® (available from Parkell, Inc., Farmindale, N.Y.), LuxaCore® Smartmix dual from DMG (available from DMG, Englewood, N.J.), and Exaflex (available from GC America, Inc., Alsip, Ill.).

In alternate embodiments, a stiffening member may be conditionally activated when exposed to air or light, placed in contact with skin, attached to the sensor site, conformed to fit to the sensor site, subjected to a specific environmental condition (e.g., when exposed to body or room temperatures), subjected to a specific chemical reaction, programmed by software, or subjected to external force, (e.g., from the tissue being probed by the sensor). For example, a conditionally activated stiffening member may be a vacuum-packed polymer that forms a rigid precipitate upon exposure to oxygen or water vapor. In other embodiments, the stiffening member may include a light curing adhesive such as Loctite® Flashcure-4305 (available from Henkel, Rocky Hill, Conn.). In another embodiment, the stiffening member may include a material undergoes a chemical hardening, such a crystallization upon exposure to a crystal seed. One such material is supersaturated sodium acetate solution that is exposed to a sodium acetate crystal. Other suitable materials for forming conditionally activated stiffening members include polyurethane and polystyrene foams that, for example, may expand and stiffen upon exposure to air.

FIG. 7 illustrates an alternate embodiment of the invention in which the stiffening member is a sleeve 92 that may be applied to a sensor, generically identified as a sensor 10, in order to mechanically stabilize the distance between the emitter 94 and detector 96 after application of the sensor 10. The sleeve 94 may have interior bumps or protrusions such as foam bumpers 95, which serve to absorb shock and cushion the sensor 10 against external forces.

Figure 8B:
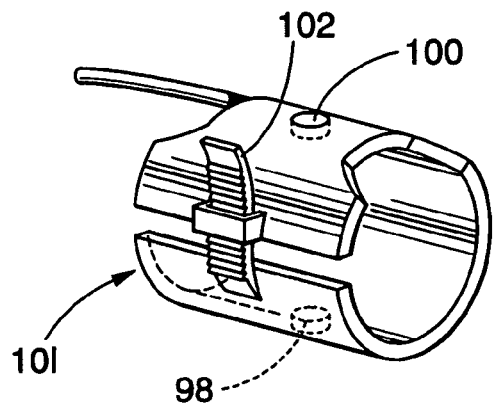
FIG. 8B illustrates a perspective view of the pulse oximetry sensor of FIG. 8A with an adjustment strap.

Although the previously discussed embodiments have described conformable sensors, it is also envisioned that similar advantages may be realized by configuring relatively rigid sensors to hold an emitter and a detector at a fixed optical distance. For example, FIG. 8A shows a rigid annular sensor 10I adapted to be applied to a patient's digit. The sensor 10I is adapted to be slid onto a patient digit, and may be further secured by a bandage or adhesive. The rigidity of the sensor 10I serves to hold the emitter 98 and the detector 100 at a fixed optical distance. In another embodiment (not shown), the sensor 10G may open at a hinge and also have a latch, snap, or other closing mechanism. The annular sensor 10I may be adjusted with a strap 102, as shown in FIG. 8B, or other adjustment mechanism in order to closely conform to the digit.

Figure 9:
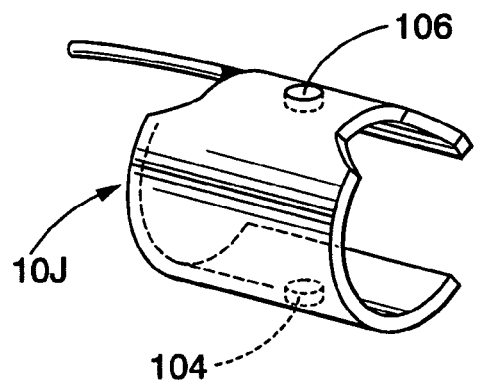
FIG. 9 illustrates an embodiment of an exemplary partially annular pulse oximetry sensor according to the present invention.

FIG. 9 shows a partially annular sensor 10J that may be placed on a digit and self-secured or secured by a bandage or other means. The sensor 10J is generally at least hemi-annular in order to provide sufficient grip on the digit. An emitter 104 and a detector 106 are arranged such that, when the sensor is applied to the digit, they would be on opposite sides of the digit.

The annular or partially annular sensors (e.g. sensors 10I and 10J) may be constructed from plastic, metal, cardboard, or any other suitable resilient material. It is contemplated the sensors 10I and 10J may be sized to approximately correlate to the profile of a jewelry ring. Alternatively, the sensors 10I and 10J may be sized to approximately correlate to the size of the first finger joint, such that when a sensor 10I or 10J is applied to the digit, the fingernail region of a digit is generally covered by the sensor, but the sensor does not interfere with flexing or bending of the finger joint. The sensors 10I and 10J may be reflectance or transmission style.

Figure 10:
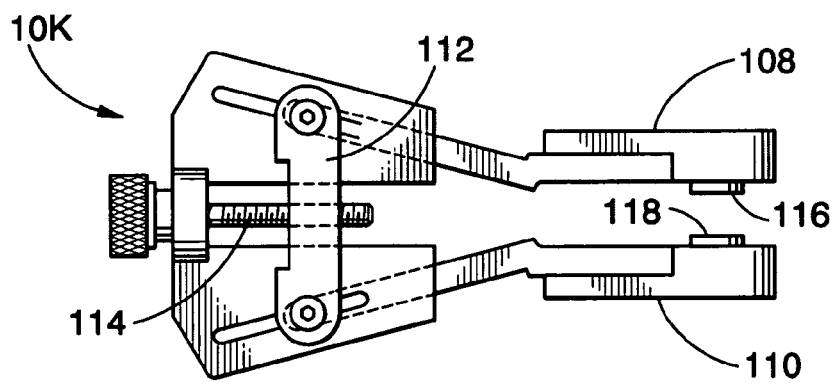
FIG. 10 illustrates a cross-sectional view of an exemplary clip-style pulse oximetry sensor with a spacer that moves to adjust the distance between the two portions of the clip.

In another embodiment, a reusable clip-style sensor adapted for use on either a digit or an earlobe is provided that holds an emitter and detector at a fixed optical distance with the use of a spacer. Such a sensor adapted for use on a patient earlobe is shown in FIG. 10, which illustrates a sensor 10K having a first portion 108 and a second portion 110 that may be moved towards one another or away from one another. The first portion 108 and the second portion 110 are each able to engage a spacer 112 that is controlled by a threaded pin 114. The spacer 112 controls the distance between the first portion 88 and the second portion 110 as the threaded pin 114 moves the spacer 112 along an angled track. The first portion 108 has an emitter 116 disposed on the tissue-contacting surface and the second portion 110 has a detector 118 disposed on the tissue-contacting surface. When the sensor 10K is applied an earlobe, the spacer 112 may be adjusted such that the sensor 10K provides a desired amount of tension to the earlobe while maintaining a fixed optical distance between the first portion 108 and the second portion 110.

An alternate embodiment of a clip-style sensor 10L with a spacer is depicted in FIG. 11A. As shown, a first portion 120 and a second portion 122 of the sensor 10L may be fixed in place after application to an earlobe with a removable spacer 124. The removable spacer 124 slides into a space 106 between the first portion 120 and the second portion 122 and prevents the first portion 120 and the second portion 122 from moving relative to one another. As shown in FIG. 11B, the removable spacer has grooves 128 and 130 into which suitably sized regions of the first portion 120 and the second portion 122 may slide. When the first portion 120 and the second portion 122 are fixed in grooves 128 and 130, they are unable to move relative to one another. The removable spacer 124 is shown with an angled profile, but may be shaped or sized in any suitable configuration that serves to hold the first portion 120 and the second portion 122 at a fixed optical distance when the spacer 124 is engaged. The removable spacer 124 may be further fixed in place magnetically (not shown).

Alternatively, in FIG. 12, a sensor 10M is illustrated in which the distance between a first portion 132 and a second portion 134 of the clip-style sensor 10M is controlled by a sliding pin 136. The sliding pin 136 and the first portion 132 and the second portion 114 are partially enclosed within a housing 137. The first portion 132 and the second portion 134 have attachment slots 138 that are able to engage the sliding pin 136. Thus, when the sliding pin 136 is pulled, the first portion 132 and the second portion 134 move towards one another. When the sliding pin 136 is pushed, the first portion 132 and the second portion 134 move away from one another. The first portion 132 and the second portion 134 may be adapted to house an emitter and a detector (not shown). To apply the sensor 10M to the patient, the sliding pin 136 is pushed into the housing 137 to increase the distance between the first portion 132 and the second portion 134 in order to accommodate the patient's tissue. The sliding pin 136 may then be pushed into the housing 137 until the desired pressure from the sensor 10M on the patient's tissue is reached.

Figure 13:
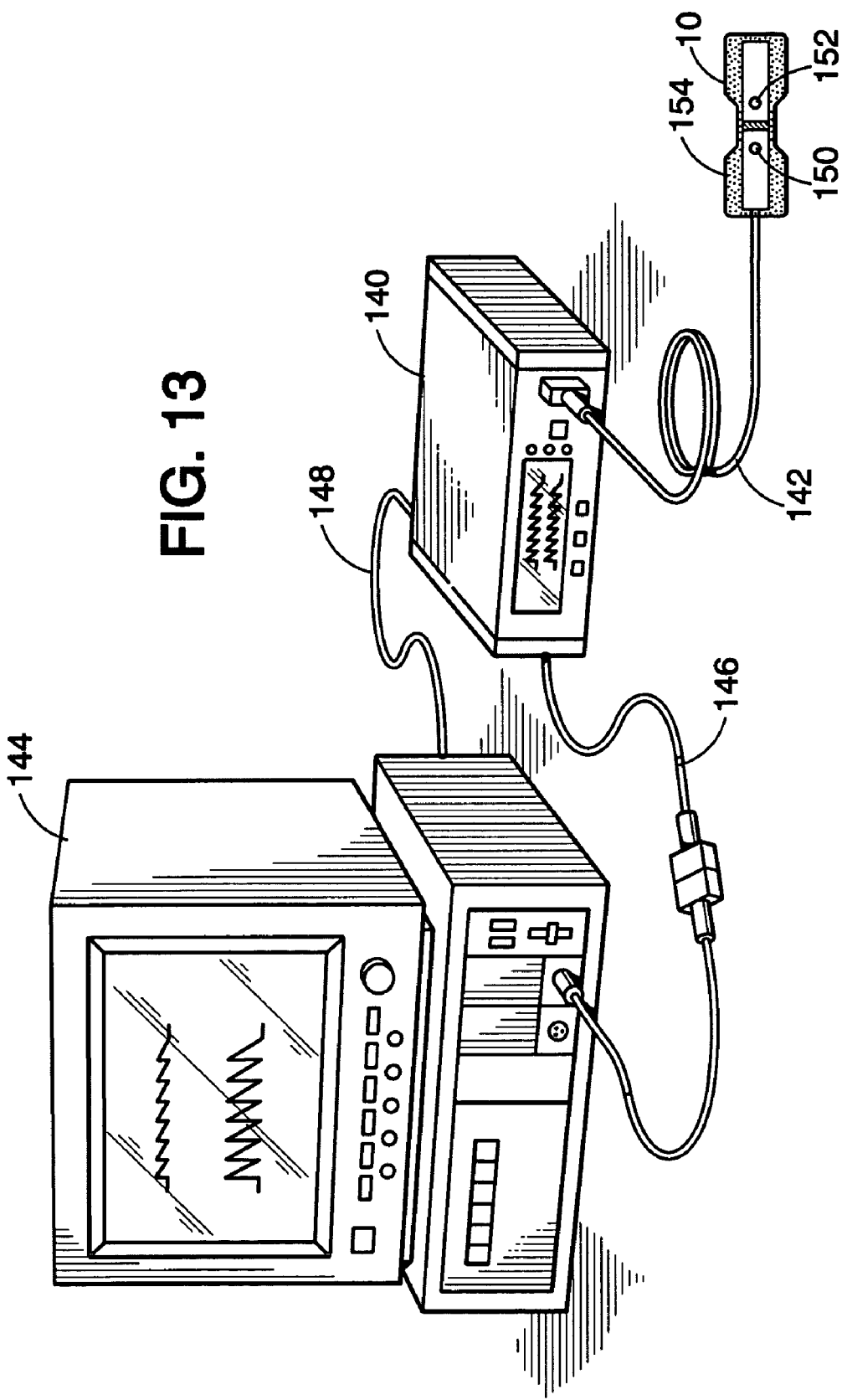
FIG. 13 illustrates a pulse oximetry system coupled to a multi-parameter patient monitor and a sensor according to embodiments of the present invention.

A sensor, illustrated generically as a sensor 10, may be used in conjunction with a pulse oximetry monitor 140, as illustrated in FIG. 13. It should be appreciated that the cable 142 of the sensor 10 may be coupled to the monitor 140 or it may be coupled to a transmission device (not shown) to facilitate wireless transmission between the sensor 10 and the monitor 140. The monitor 140 may be any suitable pulse oximeter, such as those available from Nellcor Puritan Bennett Inc. Furthermore, to upgrade conventional pulse oximetry provided by the monitor 140 to provide additional functions, the monitor 140 may be coupled to a multi-parameter patient monitor 144 via a cable 146 connected to a sensor input port or via a cable 148 connected to a digital communication port.

The sensor 10 includes an emitter 150 and a detector 152 that may be of any suitable type. For example, the emitter 150 may be one or more light emitting diodes adapted to transmit one or more wavelengths of light in the red to infrared range, and the detector 152 may one or more photodetectors selected to receive light in the range or ranges emitted from the emitter 150. Alternatively, an emitter 150 may also be a laser diode or a vertical cavity surface emitting laser (VCSEL). An emitter 150 and detector 152 may also include optical fiber sensing elements. An emitter 150 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor 10 may sense light detected from the tissue is at a different wavelength from the light emitted into the tissue. Such sensors may be adapted to sense fluorescence, phosphorescence, Raman scattering, Rayleigh scattering and multiphoton events or photoacoustic effects. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 150 and the detector 152 may be disposed on a sensor body 154, which may be made of any suitable material, such as plastic, foam, woven material, or paper. Alternatively, the emitter 150 and the detector 152 may be remotely located and optically coupled to the sensor 10 using optical fibers. In the depicted embodiments, the sensor 10 is coupled to a cable 142 that is responsible for transmitting electrical and/or optical signals to and from the emitter 150 and detector 152 of the sensor 10. The cable 142 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 150 and detector 152 that are typically placed on opposing sides of the sensor site. If the sensor site is a fingertip, for example, the sensor 10 is positioned over the patient's fingertip such that the emitter 150 and detector 152 lie on either side of the patient's nail bed. In other words, the sensor 10 is positioned so that the emitter 150 is located on the patient's fingernail and the detector 152 is located 180° opposite the emitter 150 on the patient's finger pad. During operation, the emitter 150 shines one or more wavelengths of light through the patient's fingertip and the light received by the detector 152 is processed to determine various physiological characteristics of the patient. In each of the embodiments discussed herein, it should be understood that the locations of the emitter 150 and the detector 152 may be exchanged. For example, the detector 152 may be located at the top of the finger and the emitter 150 may be located underneath the finger. In either arrangement, the sensor 10 will perform in substantially the same manner.

Reflectance type sensors also operate by emitting light into the tissue and detecting the light that is transmitted and scattered by the tissue. However, reflectance type sensors include an emitter 150 and detector 152 that are typically placed on the same side of the sensor site. For example, a reflectance type sensor may be placed on a patient's fingertip or forehead such that the emitter 150 and detector 152 lay side-by-side. Reflectance type sensors detect light photons that are scattered back to the detector 152. A sensor 10 may also be a "transflectance" sensor, such as a sensor that may subtend a portion of a baby's heel.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood and/or tissue constituents using principles of pulse oximetry. For example, using the same, different, or additional wavelengths, the present techniques may be utilized for the measurement and/or analysis of carboxyhemoglobin, methemoglobin, total hemoglobin, fractional hemoglobin, intravascular dyes, and/or water content. Rather, the invention is to cover all modifications, equivalents, and alternatives falling within the spirit and scope of the invention as defined by the following appended claims.

What is claimed is:

1. A sensor comprising:
   a substantially annular or partially annular rigid sensor body configured to retain the sensor on a patient's digit, wherein the sensor body forms a tissue-contacting surface of the sensor; and
   an emitter and a detector disposed on the tissue-contacting surface of the sensor body, wherein the sensor body is adapted to hold the emitter and detector at a fixed optical distance relative to one another and relative to the patient's digit when the sensor is attached to a patient and when the sensor experiences an external tapping force or when the digit applies a flexing force to the sensor.

2. The sensor, as set forth in claim 1, wherein the sensor body is adapted to have an adjustable diameter.

3. The sensor, as set forth in claim 1, wherein the sensor body comprises an adjustment strap.

4. The sensor, as set forth in claim 3, wherein the adjustment strap comprises a plurality of notches adapted to fix the diameter of the sensor body.

5. The sensor, as set forth in claim 1, wherein the sensor body comprises a hinge.

6. The sensor, as set forth in claim 1, wherein the emitter and the detector are adapted to operate in a transmission mode.

7. The sensor, as set forth in claim 1, wherein the emitter and the detector are adapted to operate in a reflectance mode.

8. The sensor, as set forth in claim 1, wherein the sensor body is adapted to allow flexing of an adjacent finger joint when applied to a fingernail region of a finger.

9. The sensor, as set forth in claim 1, wherein the sensor body comprises a ring adapted to allow flexing of an adjacent finger joint when applied to a finger or toe.

10. The sensor, as set forth in claim 1, wherein an adhesive is disposed on the sensor body to couple the sensor body to the digit.

11. A pulse oximetry system comprising:
    a pulse oximetry monitor; and
    a pulse oximetry sensor adapted to be operatively coupled to the monitor, the sensor comprising:
       a substantially annular or partially annular rigid sensor body configured to retain the sensor on a patient's digit, wherein the sensor body forms a tissue-contacting surface of the sensor; and
       an emitter and a detector disposed on the tissue-contacting surface of sensor body, wherein the sensor body is adapted to hold the emitter and detector at a fixed optical distance relative to one another and relative to the patient's digit when the sensor is attached to a patient and when the digit applies a flexing force to the sensor or when an external tapping force is applied to the sensor.

12. The system, as set forth in claim 11, wherein the emitter and the detector are adapted to operate in transmission mode.

13. The system, as set forth in claim 11, wherein the emitter and the detector are adapted to operate in reflectance mode.

14. The system, as set forth in claim 11, wherein the sensor body is adapted to have an adjustable diameter.

15. The system, as set forth in claim 11, wherein the sensor body comprises an adjustment strap.

16. The system, as set forth in claim 11, wherein the sensor body comprises a hinge.

17. A method of manufacturing a pulse oximetry sensor adapted to be applied to a digit, comprising:
    providing an annular or partially annular rigid sensor body configured to retain the sensor on the digit and wherein an emitter and a detector are disposed on the tissue-contacting surface of the sensor body, wherein the sensor body is adapted to hold the emitter and the detector at a fixed optical distance relative to each other and relative to the digit when the sensor experiences an external tapping force or when the digit applies a flexing force to the sensor.

18. The method, as set forth in claim 17, comprising:
    providing an adjustment strap.

19. The method, as set forth in claim 17, comprising:
    providing a hinge in the sensor body.

20. The method, as set forth in claim 17, wherein the emitter and the detector are adapted to operate in transmission mode.

21. The method, as set forth in claim 17, wherein the emitter and the detector are adapted to operate in reflectance mode.

* * * * *